US009488707B2

(12) United States Patent
Kobayashi et al.

(10) Patent No.: US 9,488,707 B2
(45) Date of Patent: Nov. 8, 2016

(54) METHOD FOR PREDICTING RESISTANCE TO HEAT DETERIORATION OF ISOPRENE RUBBER

(71) Applicant: SUMITOMO RUBBER INDUSTRIES, LTD., Kobe-shi, Hyogo (JP)

(72) Inventors: Masatoshi Kobayashi, Kobe (JP); Yasuhisa Minagawa, Kobe (JP)

(73) Assignee: SUMITOMO RUBBER INDUSTRIES, LTD., Kobe-Shi (JP)

( * ) Notice: Subject to any disclaimer, the term of this patent is extended or adjusted under 35 U.S.C. 154(b) by 856 days.

(21) Appl. No.: 13/829,595

(22) Filed: Mar. 14, 2013

(65) Prior Publication Data
US 2013/0335078 A1 Dec. 19, 2013

(30) Foreign Application Priority Data
Jun. 13, 2012 (JP) .................. 2012-134104

(51) Int. Cl.
*G01R 33/46* (2006.01)
*G01N 24/08* (2006.01)

(52) U.S. Cl.
CPC ............. *G01R 33/46* (2013.01); *G01N 24/08* (2013.01)

(58) Field of Classification Search
CPC ................... G01R 33/46; G01N 24/08
See application file for complete search history.

(56) References Cited

U.S. PATENT DOCUMENTS

| 7,402,437 B2 * | 7/2008 | Gonzalez | G01N 1/42 324/307 |
| 8,178,621 B2 * | 5/2012 | Kim | C08G 73/10 525/150 |
| 2011/0311899 A1 * | 12/2011 | Onodera | C08G 61/12 429/482 |

FOREIGN PATENT DOCUMENTS

JP 2004-325189 A 11/2004

* cited by examiner

*Primary Examiner* — Dixomara Vargas
(74) *Attorney, Agent, or Firm* — Birch, Stewart, Kolasch & Birch, LLP

(57) ABSTRACT

A method for predicting the resistance to heat deterioration of a sulfur-vulcanized isoprene rubber is disclosed. The nuclear magnetic resonance spectrum of the isoprene rubber is obtained by the use of a solid state nuclear magnetic resonance method employing magic angle spinning. The spectrum of a cross-linked structure α and the spectrum of a cross-linked structure β in the nuclear magnetic resonance spectrum are identified. The percentage of the cross-linked structure α and the percentage of the cross-linked structure β in the overall cross-linked structures of the sulfur are computed from the spectrum. From the computed percentages, the resistance to heat deterioration of the isoprene rubber is predicted.

11 Claims, 2 Drawing Sheets chemical shift (ppm)
resonant frequency: 920 MHz chemical shift (ppm)
resonant frequency: 500 MHz

METHOD FOR PREDICTING RESISTANCE TO HEAT DETERIORATION OF ISOPRENE RUBBER

BACKGROUND OF THE INVENTION

The present invention relates to a method for predicting the resistance to heat deterioration of a sulfur-vulcanized isoprene rubber, more particularly to a prediction method utilizing a solid state nuclear magnetic resonance method employing magic angle spinning by which the resistance to heat deterioration can be predicted with high accuracy.

Heretofore, the resistance to heat deterioration of a sulfur-vulcanized isoprene rubber was evaluated by the ratio of polysulphide in which plural sulfur atoms bridge between polymer chains and monosulphide in which one sulfur atom bridges between polymer chains, obtained through an experiment for example according to swelling compressive method.

As to the heat resistance and heat deterioration, the monosulphide is superior to the polysulphide. Therefore, the resistance to heat deterioration can be estimated roughly from the ratio of the polysulphide and the monosulphide in the rubber.

In the swelling compressive method, the vulcanized rubber is swollen, and the swollen rubber is compressed by applying a load. Then, the measured compressive stress and strain are applied to FLORY's relationship, and the mesh density is obtained as the overall crosslink density.

Further, the rubber is subjected to a chemical treating to cut —S—S— link by the use of lithium aluminum hydride. The treated rubber is compressed by applying a load, and the measured compressive stress and strain are applied to FLORY's relationship, and the mesh density is obtained as the crosslink density of the monosulphide. Then, by subtracting this density from the overall crosslink density, the crosslink density of the polysulphide is obtained.

In this way, the above-mentioned ratio of the polysulphide and the monosulphide can be obtained as the ratio of the crosslink density of the polysulphide and the crosslink density of the monosulphide.

It is however difficult to accurately evaluate the resistance to heat deterioration from the empirically-obtained ratio of the polysulphide and the monosulphide.

SUMMARY OF THE INVENTION

It is therefore, an object of the present invention to provide a method for predicting the resistance to heat deterioration of isoprene rubber with accuracy.

According to the present invention, a method for predicting resistance to heat deterioration of a sulfur-vulcanized isoprene rubber, comprises:

measuring a nuclear magnetic resonance spectrum of the isoprene rubber by the use of a solid state nuclear magnetic resonance method employing magic angle spinning, identifying, in the nuclear magnetic resonance spectrum, a cross-linked structure α in which no double link exist near the reaction point of sulfur and a cross-linked structure β in which a double link exists near the reaction point of sulfur, obtaining, from the nuclear magnetic resonance spectrum, the ratio of the cross-linked structure α and the ratio of the cross-linked structure β to the total cross-linked structures of sulfur, and predicting the resistance to heat deterioration of the isoprene rubber, based on the obtained ratios.

In the magic angle spinning, the rotation frequency of the specimen of the isoprene rubber is preferably set to a value in a range of from about 16 to 17 kHz.

In the nuclear magnetic resonance method, the resonant frequency of hydrogen nucleus ($^1$H) is preferably not less than 600 MHz.

In the process of predicting the resistance to heat deterioration, it is preferred that the spectrum area Sa of the cross-linked structure α and the spectrum area Sb of the cross-linked structure β are computed, and based on the ratio Sa/Sb of the spectrum area Sa to the spectrum area Sb, the resistance to heat deterioration is determined.

The carbon-sulfur dissociation energy of the cross-linked structure α is higher than the carbon-sulfur dissociation energy of the cross-linked structure β. As a result, the cross-linked structure α is resistant to heat deterioration, and the cross-linked structure β is poor at heat deterioration. According to the present Invention, the ratios of the cross-linked structure α and the cross-linked structure β in the overall cross-linked structures of sulfur can be obtained with accuracy, Therefore, without experimentally measuring the ratios of the monosulphide and polysulphide, the resistance to heat deterioration of the isoprene rubber can be predicted with accuracy.

DESCRIPTION OF THE PREFERRED EMBODIMENTS

Embodiments of the present invention will now be described in detail in conjunction with accompanying drawings.

In the method according to the present invention, the resistance to heat deterioration of a sulfur-vulcanized isoprene rubber is predicted by the use of a solid state nuclear magnetic resonance method employing magic angle spinning.

Here, the sulfur-vulcanized isoprene rubber includes synthetic isoprene rubber and natural rubber vulcanized by adding sulfur.

In order to perform the nuclear magnetic resonance, a solid state nuclear magnetic resonance apparatus is used. A known apparatus can be used.

In this embodiment, firstly, a measuring process for obtaining the nuclear magnetic resonance spectrum of the isoprene rubber is performed.

In the measuring process, a solid-state sample tube of a diameter 4 mm for example is filled with the solid isoprene rubber. The tube is set in the solid state nuclear magnetic resonance apparatus.

Figure 1A:
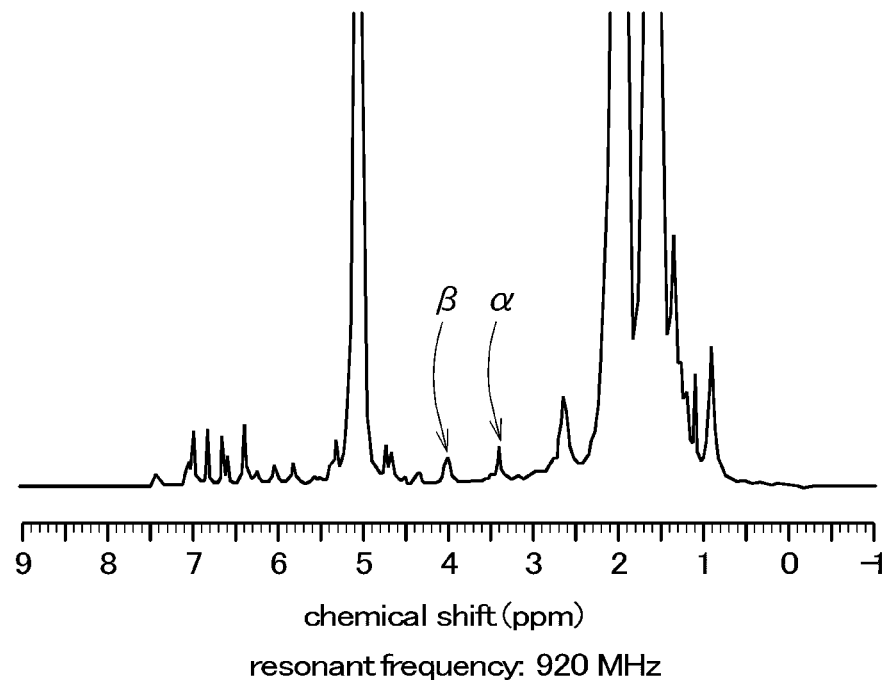
FIG. 1(a) shows nuclear magnetic resonance spectrum of hydrogen nucleus ($^1$H) at resonant frequency 920 MHz.
Figure 1B:
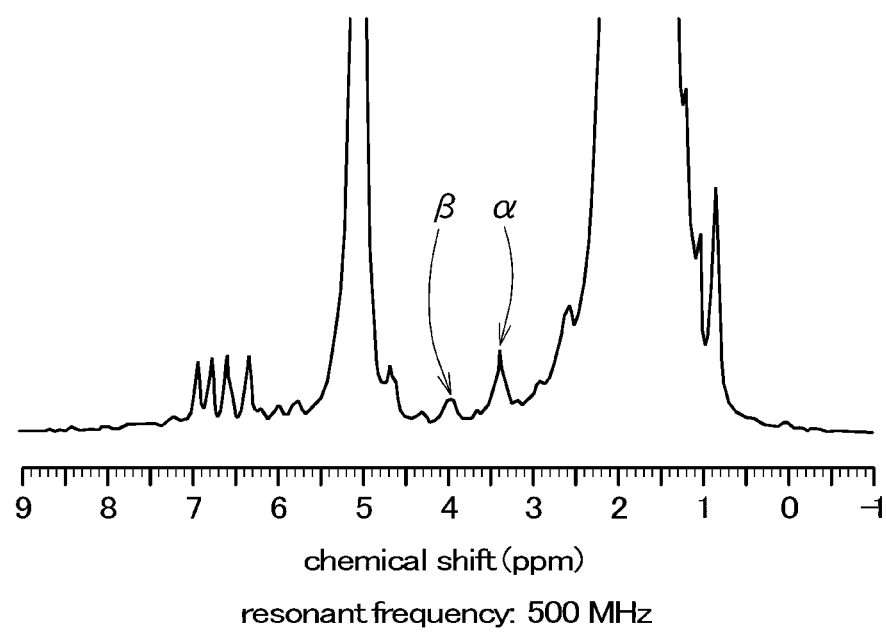
FIG. 1(b) shows nuclear magnetic resonance spectrum of hydrogen nucleus ($^1$H) at resonant frequency 500 MHz.

The nuclear magnetic resonance spectrum of hydrogen nucleus ($^1$H) of the isoprene rubber (namely, frequency spectra of magnetic resonance signals from the isoprene rubber) was measured with the apparatus under the following conditions: the resonant frequency of the hydrogen nucleus ($^1$H) was 920 MHz, the magic angle with respect to the direction of the external magnetic field was 54.7 degrees, and
the rotation frequency of the sample tube was 17 kHz. In FIG. 1(*a*), an example of the obtained frequency spectra of magnetic resonance signals from the isoprene rubber is shown.

Next, in the obtained frequency spectra, spectra of the following cross-linked structures are identified:
a cross-linked structure α in which no double link exist near the reaction point of sulfur, and
a cross-linked structure β in which a double link exists near the reaction point of sulfur.

Here, the "reaction point of sulfur" means a carbon atom of the polymer (isoprene) with which a sulfur atom makes a chemical bond. The expression "near the reaction point" means a range within two covalent linkages counted from the reaction point or the carbon.

Figure 2A:
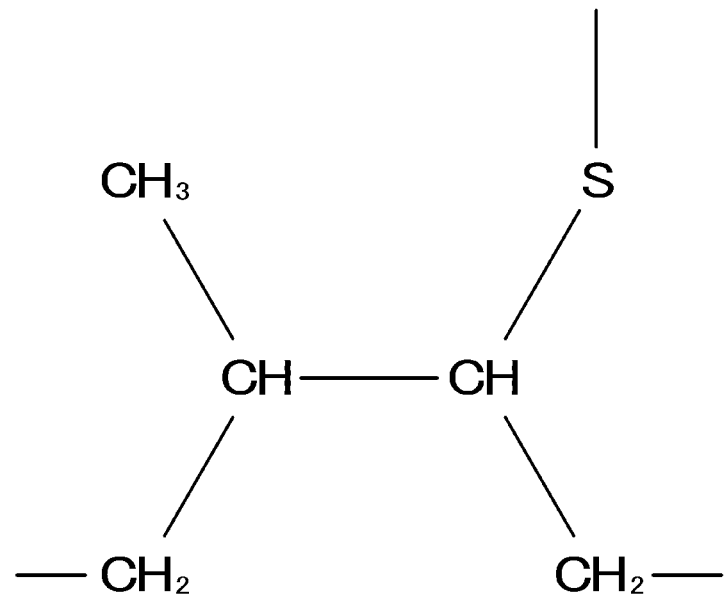
FIG. 2(a) is a construction drawing of an example of cross-linked structure α.
Figure 2B:
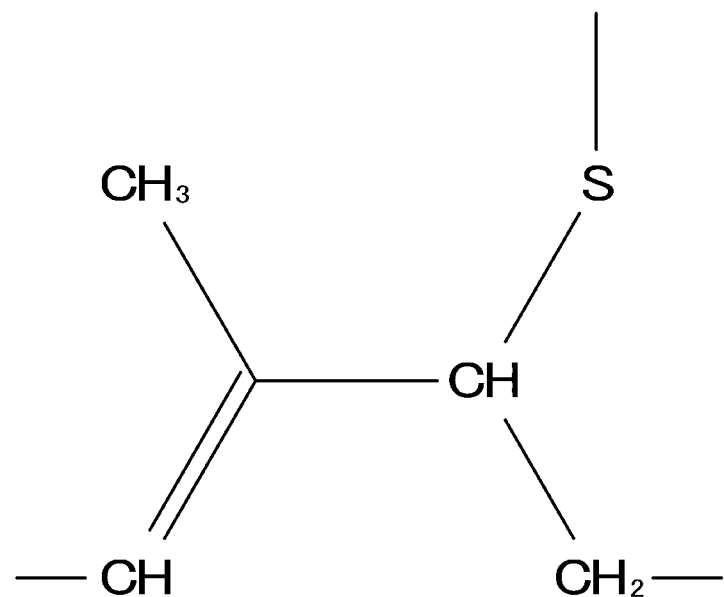
FIG. 2(b) is a construction drawing of an example of cross-linked structure β.

In the case of the cross-linked structure α (FIG. 2(*a*) shows a typical example), the carbon-sulfur dissociation energy is about 70 Kcal/mol. In the case of the cross-linked structure β (FIG. 2(*b*) shows a typical example), the carbon-sulfur dissociation energy is about 50 Kcal/mol.

Such a difference in the carbon-sulfur dissociation energy between the cross-linked structures α and β is caused by whether double links exist or not. When compared with a compound having no double link near the reaction point, a compound having double link near the reaction point is increased in the carbon-sulfur dissociation energy by about 20 Kcal/mol.

In the frequency spectra, owing to the difference in the carbon-sulfur dissociation energy, the cross-linked structure α and the cross-linked structure β can be identified, as shown in FIG. 1, at difference locations of a chemical shift of about 3.4 ppm and a chemical shift of about 4.0 ppm.

In the frequency spectra, tetramethylsilane is used as the reference substance for the chemical shift of 0 ppm.

Next, a predicting process is performed. In the predicting process, a ratio of the cross-linked structure α and a ratio of the cross-linked structure β to the overall cross-linked structures of sulfur are obtained, and, based on these ratios, the resistance to heat deterioration of the isoprene rubber is predicted.

The cross-linked structure α is resistant to heat deterioration because no double link exists near the reaction point of sulfur. In contrast, the cross-linked structure β is poor at heat deterioration because double link exists near the reaction point of sulfur. Therefore, the resistance to heat deterioration of the isoprene rubber can be predicted from the above-mentioned ratios.

The predicting process comprises a process in which the spectrum area Sa of the cross-linked structure α is computed, and a process in which the spectrum area Sb of the cross-linked structure β is computed.

In this embodiment, more specifically, with respect to the nuclear magnetic resonance spectrum of the hydrogen nucleus ($^1$H) of the isoprene rubber, the spectrum area Sa of the spectrum peak (if any) of the cross-linked structure α located at the chemical shift of about 3.4 ppm, and the spectrum area Sb of the spectrum peak (if any) of the cross-linked structure β located at the chemical shift of about 4.0 ppm are computed.

Further, in the predicting process, the ratio Sa/Sb is computed. The ratio Sa/Sb can be used directly to relatively compare the resistance to heat deterioration with that of another isoprene rubber in order to decide which is better. Further, by referencing the ratio Sa/Sb to a referencing table presenting the relationship between the ratio Sa/Sb and the resistance to heat deterioration experimentally obtained beforehand, the resistance to heat deterioration of the isoprene rubber can be predicted absolutely.

Assuming that the spectral curve of each spectrum peak accords with Lorenz curve, the respective spectrum peaks can be separated from each other.

Based on the separated spectral curve, the spectrum area Sa, Sb can be obtained by the use of the following Lorenz function:

$$L(\omega) = r^2 / (r^2 + (\omega 0 - \omega)^2)$$

where
$\omega 0$ is the resonant frequency at the concerned peak, and
r is one half of the peak width at half height.

Here, the "peak width at half height" is the frequency width of the spectral curve of the concerned spectrum peak measured at one half of the max height of the spectrum peak.

In this embodiment, it is desirable that the resonant frequency of the hydrogen nucleus ($^1$H) which is set to the nuclear magnetic resonance apparatus, is not less than 600 MHz in order to increase the resolving power in the nuclear magnetic resonance spectrum of the hydrogen nucleus ($^1$H).

If the resonant frequency is less than 600 mHz, the resolving power is decreased as shown in FIG. 1(*b*), and it becomes difficult to accurately compute the spectrum area Sa and Sb. Since the spectral resolution is improved with the increase in the resonant frequency, it becomes possible to compute the spectrum area with high accuracy.

It is therefore preferable that the resonant frequency of the hydrogen nucleus ($^1$H) is not less than 800 MHz, more preferably not less than 900 MHz.

In the spectrum shown in FIG. 1(*a*), there are many peaks near 2 ppm whereas in the spectrum shown in FIG. 1(*b*), there are few peaks near 2 ppm. Thus, in comparison with FIG. 1(*a*), the resolving power in FIG. 1(*b*) is low.

If the resonant frequency is less than 600 mHz, as shown in FIG. 1(*b*), the spectrum peak of the cross-linked structure α, β probably overlaps with a spectrum peak of another nearby component (compound), and it becomes difficult to accurately compute the spectrum area Sa, Sb.

In the magic angle spinning which is employed in the solid state nuclear magnetic resonance method in this embodiment, the sample tube filled with the isoprene rubber specimen has to be rotated in an inclined state such that the rotational axis of the sample tube is inclined at an angle of 54.7 degrees with respect to the direction of the external magnetic field in order to reduce dipole-dipole ($^1$H-$^1$H) interactions and thereby improve the spectral resolution.

Further, in order to improve the spectral resolution by reducing the chemical shift anisotropy and the broadening of spectral line (peak) due to the dipole-dipole interactions, the rotation frequency of the sample tube in the magic angle spinning is preferably set to not less than 16 kHz, more preferably not less than 17 kHz. For example, the rotation frequency is set to 16+/−0.1 kHz (15900 to 16100 revolutions per second).

Further, in addition to the use of the above described magic angle spinning, it is preferred to use a decoupling high-frequency magnetic field which is applied to the hydrogen nucleus ($^1$H) (specimen) in order to allow magnetization transfer between nuclear spins.

The resistance to heat deterioration is affected by the ratios of the cross-linked structure α and the cross-linked structure β as well as the ratio of the polysulphide and the monosulphide as explained above.

Therefore, the method according to the present invention is most effectual when used to compare the resistances to heat deterioration of rubber compounds having substantially same ratios of the polysulphide and the monosulphide. (For example, the variation of the ratio in % of the monosulphide (crosslink density) and the polysulphide (crosslink density) are within +/−5 points, more preferably +/−2 points.)

As a results, the influence of the ratio of the polysulphide and the monosulphide is minimized, and a more accurate comparative analysis is possible.

Comparison Tests

The following compounding materials excepting sulfur and vulcanizing accelerator were kneaded by the use of a 1.7 liter banbury mixer, and then sulfur and vulcanizing accelerator were added and the compounding materials were kneaded by the use of open rollers for three minutes in a temperature range of from 80 to 90 deg. C. Thereby, unvulcanized rubber was prepared.

<Composition>
Isoprene rubber: 100 parts by weight (Nipol IR2200, ZEON corporation)
Zinc oxide: 3 parts by weight (zinc oxide second grade, Mitsui Mining & smelting Co., Ltd.)
Stearic acid: 2 parts by weight (TSUBAKI, beads, NOF Corporation)
Age resistor: 2 parts by weight (Santoflex 6PPD, FLEX-SYS)
Furnace black (ISAF): 50 parts by weight (DIABLACK, Mitsubishi Chemical Corporation) (N2SA: 114 m^2/g)
Sulfur: powdered sulfur (size: 200 meshes), Tsurumi Chemical Industry Co., Ltd.
Vulcanizing accelerator: tetraethylthiuramdisulfide, NOC-CELER TET, Ouchi Shinko Chemical Industrial Co., Ltd., The unvulcanized rubber prepared as above was press vulcanized at 170 deg. C for 10 to 20 minutes.

By changing the contents of sulfur and vulcanizing accelerator, plural kinds of vulcanized rubbers different from each other in respect to the ratio Sa/Sb of the spectrum areas of the cross-linked structures α and β were prepared.

Using the above-mentioned swelling compressive method, the plural kinds of vulcanized rubbers were measured for the monosulphide/polysulphide ratio, and those having substantially same monosulphide/polysulphide ratios (55+/−2%) were selected and used in the following tests.

Using a solid state nuclear magnetic resonance apparatus (ECA920 manufactured by JEOL Ltd.) whose field strength is up to 920 mHz (magnetic field up to 21.6T), the spectrum area Sa of the cross-linked structure α and the spectrum area Sb of the cross-linked structure β were obtained as explained above under the following conditions, and
the spectrum area ratio Sa/Sb was determined.
Resonant frequency: 920 MHz,
Rotation frequency in magic angle spinning: 17 kHz,
Number of times making accumulation of magnetic resonance signals: 256
Time interval between accumulations: 5 second.

*Test 1 <Rate of Decrease in Swelling Rate>
In order to obtain the swelling rate, according to the Japanese Industrial standard K6258, the vulcanized rubber was dipped into toluene at 40 degrees C. for 24 hours to swell, and the swelling rate V1 (swelled volume/original volume) was obtained.

At the same time, the vulcanized rubber was put in a hot oven for seven days to heat deteriorate, and then its swelling rate V2 was obtained as above.

The ratio V2/V1, as the rate of decrease in the swelling rate, is shown in Table 1. The smaller the ratio V2/V1, the more the heat deterioration is.

*Test 2 <Rate of Increase in Stress at 100% Elongation>
As to the stress (M100 MPa) at 100% elongation, the stress R1 of the vulcanized rubber (original) and the stress R2 of the vulcanized rubber heat deteriorated as explained above were measured at 23 degrees C. through a tensile test according to the Japanese Industrial Standard K6251 using a No. 3 type dumbbell specimen and a tension rate of 500 mm/minute.

The ratio R2/R1, as the rate of increase in the stress at 100% elongation, is shown Table 1. The larger the ratio R2/R1, the more the heat deterioration is.

TABLE 1

| Isoprene rubber | No. 1 | No. 2 | No. 3 | No. 4 | No. 5 |
| --- | --- | --- | --- | --- | --- |
| Sa/Sb ratio | *1 | 5.4 | 3.7 | 1.0 | 0.67 |
| monosulphide/polysulphide ratio (%) | 57 | 55 | 54 | 53 | 56 |
| V2/V1 (%) | 100 | 101 | 98 | 90 | 91 |
| R2/R1 (%) | 113 | 110 | 115 | 135 | 137 |

*1) Sb = 0

From the test results, it was confirmed that there is a correlation between the resistance to heat deterioration and the spectrum area ratio of the cross-linked structures α and β.

If the spectrum area ratio Sa/Sb is decreased under 1.0, the heat deterioration increases, namely, the resistance to heat deterioration becomes worse. If the spectrum area ratio Sa/Sb is increased over 1.0 especially 3.7, the heat deterioration is decreased, namely, the resistance to heat deterioration becomes improved. Therefore, based on the spectrum area ratio Sa/Sb, the resistance to heat deterioration of isoprene rubber can be predicted with high accuracy.

The invention claimed is:

1. A method for predicting resistance to heat deterioration of a sulfur-vulcanized isoprene rubber, comprising:
   measuring a nuclear magnetic resonance spectrum of the isoprene rubber by the use of a solid state nuclear magnetic resonance method employing magic angle spinning,
   identifying, in the nuclear magnetic resonance spectrum, a cross-linked structure α in which no double link exist near the reaction point of sulfur and a cross-linked structure β in which a double link exists near the reaction point of sulfur,
   obtaining, from the nuclear magnetic resonance spectrum, a spectrum area Sa of the cross-linked structure α and a spectrum area Sb of the cross-linked structure β,
   predicting the resistance to heat deterioration of the isoprene rubber, based on the ratio Sa/Sb of the spectrum area Sa to the spectrum area Sb such that
   if the ratio Sa/Sb is less than a first reference value, the resistance is predicted as being not good,
   if the ratio Sa/Sb is not less than the first reference value and less than a second reference value, the resistance is predicted as being good, and
   if the ratio Sa/Sb is not less than the second reference value, the resistance is predicted as being excellent; and outputting the obtained ratio Sa/Sb and the predicted resistance in order to improve the isoprene rubber in the resistance to heat deterioration.

2. The method according to claim 1, wherein
in the process of predicting the resistance to heat deterioration, the first reference value is set to 1.0, and the second reference value is set to 3.7.

3. The method according to claim 2, wherein
the rotation frequency in the magic angle spinning is in a range of from 16 to 17 kHz.

4. The method according to claim 2, wherein
said nuclear magnetic resonance spectrum is that of hydrogen nucleus ($^1$H) measured when the resonant frequency of hydrogen nucleus ($^1$H) is not less than 600 MHz.

5. The method according to claim 2, which is applied to each of plural kinds of sulfur-vulcanized isoprene rubber compounds having different compositions and having substantially same ratios of polysulphide and monosulphide.

6. The method according to claim 1, wherein
the rotation frequency in the magic angle spinning is in a range of from 16 to 17 kHz.

7. The method according to claim 3, wherein
said nuclear magnetic resonance spectrum is that of hydrogen nucleus ($^1$H) measured when the resonant frequency of hydrogen nucleus ($^1$H) is not less than 600 MHz.

8. The method according to claim 6, which is applied to each of plural kinds of sulfur-vulcanized isoprene rubber compounds having different compositions and having substantially same ratios of polysulphide and monosulphide.

9. The method according to claim 1, wherein
said nuclear magnetic resonance spectrum is that of hydrogen nucleus ($^1$H) measured when the resonant frequency of hydrogen nucleus ($^1$H) is not less than 600 MHz.

10. The method according to claim 9, which is applied to each of plural kinds of sulfur-vulcanized isoprene rubber compounds having different compositions and having substantially same ratios of polysulphide and monosulphide.

11. The method according to claim 1, which is applied to each of plural kinds of sulfur-vulcanized isoprene rubber compounds having different compositions and having substantially same ratios of polysulphide and monosulphide.

* * * * *